United States Patent
Grodzki

(10) Patent No.: US 11,604,241 B2
(45) Date of Patent: Mar. 14, 2023

(54) METHOD AND SYSTEM OF AUTOMATIC SELECTION FOR THE SUPPRESSION OF A TISSUE COMPONENT

(71) Applicant: Siemens Healthcare GmbH, Erlangen (DE)

(72) Inventor: David Grodzki, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 32 days.

(21) Appl. No.: 16/785,955

(22) Filed: Feb. 10, 2020

(65) Prior Publication Data

US 2020/0256940 A1 Aug. 13, 2020

(30) Foreign Application Priority Data

Feb. 11, 2019 (EP) .................................... 19156482

(51) Int. Cl.
| | | |
|---|---|---|
| *G01R 33/483* | (2006.01) | |
| *G01R 33/565* | (2006.01) | |
| *G01R 33/54* | (2006.01) | |
| *A61B 5/055* | (2006.01) | |
| *A61B 5/00* | (2006.01) | |

(52) U.S. Cl.
CPC ........ *G01R 33/4838* (2013.01); *A61B 5/0033* (2013.01); *A61B 5/055* (2013.01); *G01R 33/546* (2013.01); *G01R 33/56563* (2013.01)

(58) Field of Classification Search
CPC .............. G01R 33/4838; G01R 33/546; G01R 33/56563; G01R 33/5607; G01R 33/56518; G01R 33/5659; G01R 33/543
See application file for complete search history.

(56) References Cited

U.S. PATENT DOCUMENTS

| | | | | |
|---|---|---|---|---|
| 5,856,744 A | * | 1/1999 | Block | .............. G01R 33/56518 |
| | | | | 324/309 |
| 2004/0064032 A1 | | 4/2004 | Ma | |

(Continued)

OTHER PUBLICATIONS

"CHESS/Fat-Sat Pulses" published by MRIquestions.com. 2021 (Year: 2021).*

(Continued)

*Primary Examiner* — Rishi R Patel
(74) *Attorney, Agent, or Firm* — Banner & Witcoff Ltd.

(57) ABSTRACT

In a method for automatic control of an examination sequence in magnetic resonance (MR) system during recording of MR signals in an examination segment of a person being examined, which has two tissue components with two different MR resonant frequencies, an examination sequence for examination of the examination segment is determined. Further, whether the examination sequence includes an imaging sequence in which one of the two tissue components is to be suppressed and for which at least two different suppression options exist to reduce the one of the two tissue components during the recording of the MR signals is determined. In response to the determination that the examination sequencing included the imaging sequence, the method can include determining a sequence parameter of the examination for the imaging sequence; and selecting one of the at least two suppression options as a function of the sequence parameter determined for the imaging sequence.

20 Claims, 3 Drawing Sheets

(56) References Cited

U.S. PATENT DOCUMENTS

2015/0316633 A1* 11/2015 Imamura ............ G01R 33/5607
324/322
2016/0169997 A1 6/2016 Fautz et al.
2017/0160357 A1* 6/2017 Biber ................. G01R 33/3815
2020/0072934 A1* 3/2020 Hoelscher .......... G01R 33/5607

OTHER PUBLICATIONS

Morrell, Glen, and Daniel Spielman. "Dynamic shimming for multi-slice magnetic resonance imaging." Magnetic resonance in medicine 38.3 (1997): 477-483. (Year: 1997).*

Del Grande et al., "HHS Public Access Fat-Suppression Techniques for 3-T MR Imaging of the Musculoskeletal System," RadioGraphics, vol. 34, No. 1, pp. 217-233, Jan. 2014; (https://doi.org/10.1148/rg.341135130); (https://www.ncbi.nlm.nih.gov/pmc/articles/PMC4359893/).

Search Report from European Patent Office, dated Aug. 14, 2019, for Application No. 19156482.2.

* cited by examiner

FIG 2
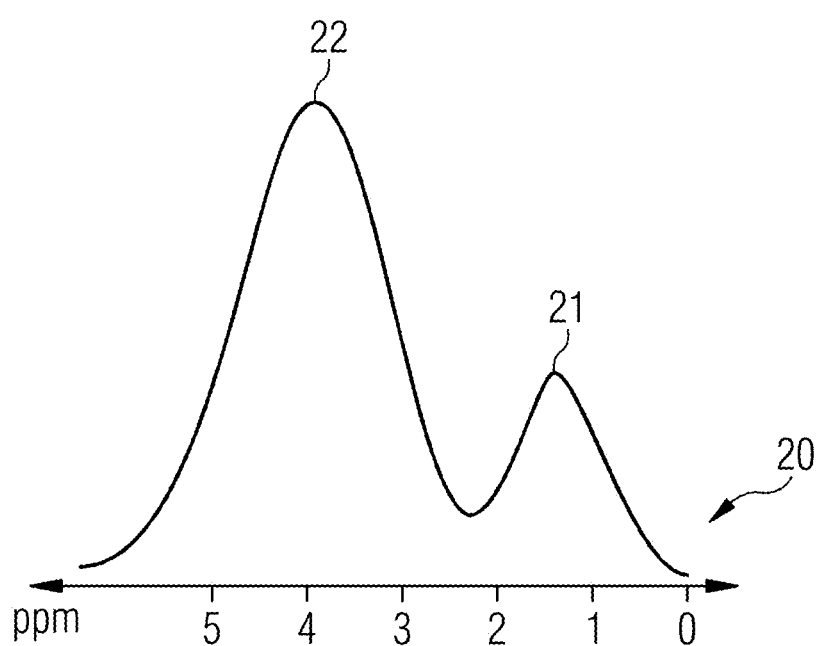
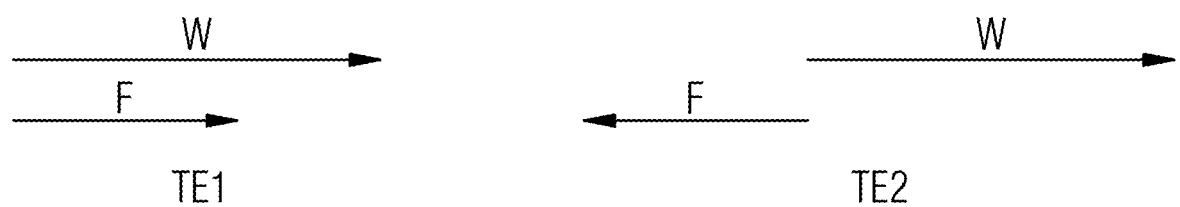

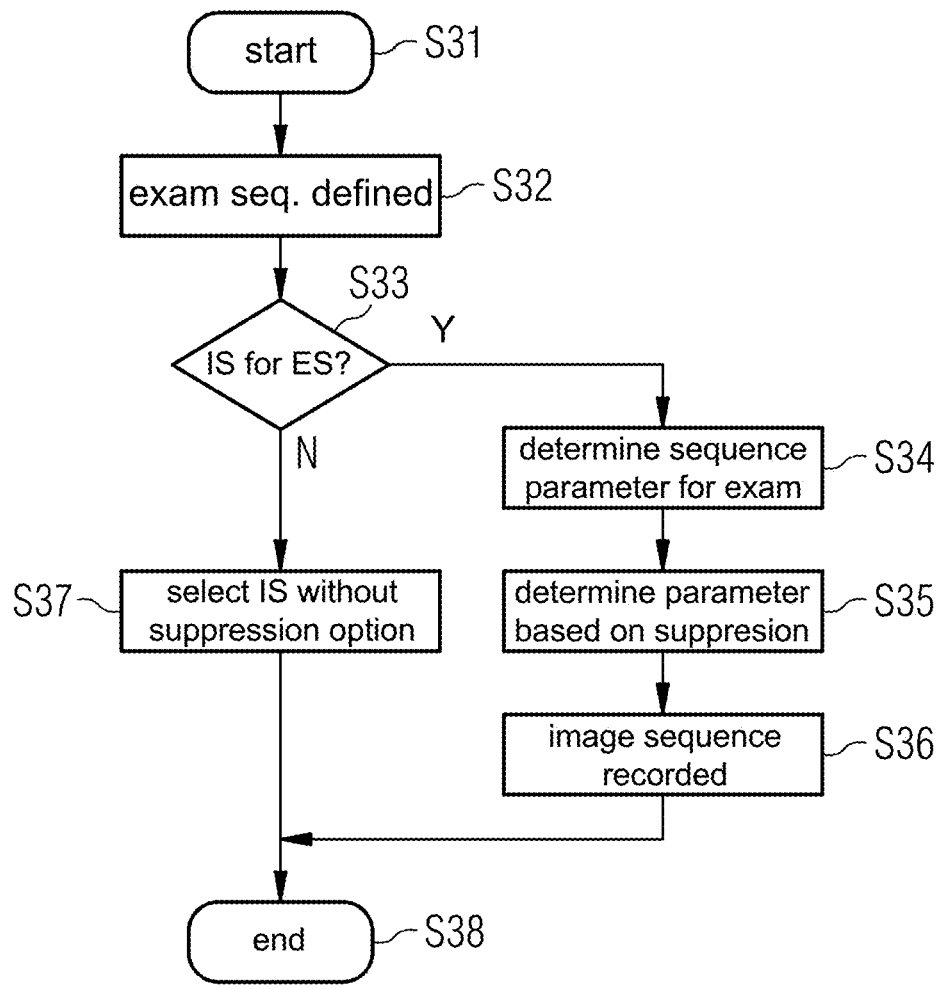
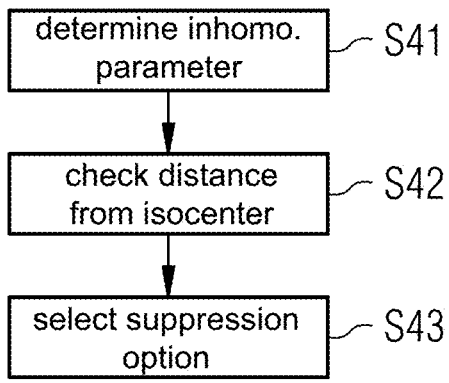

METHOD AND SYSTEM OF AUTOMATIC SELECTION FOR THE SUPPRESSION OF A TISSUE COMPONENT

CROSS REFERENCE TO RELATED APPLICATIONS

This patent application claims priority to European Patent Application No. 19156482.2, filed Feb. 11, 2019, which is incorporated herein by reference in its entirety.

BACKGROUND

Field

The present disclosure relates to a method for automatic control of an examination sequence in a Magnetic Resonance (MR) system in an examination segment that has two tissue components with two different MR resonant frequencies. Furthermore provided is the associated MR system, a computer program with program media and an electronically readable data medium.

Related Art

A great advantage of MRT (Magnetic Resonance Tomography) by comparison with x-ray-based methods such as Computed Tomography CT for example is the high soft tissue contrast that is possible with MRT. Depending on the issues involved, various weightings can be undertaken, which make an optimal display of the tissue possible. The human body has areas in which fat signal components and water signal components are present in the MR signal. Fat and water have a different resonant frequency. For a few medical issues a suppression of the fat signal is desirable. Mostly a spectrally selective and/or a T1-selective RF preliminary pulse is used to do this or the DIXON method is used, which is based on the fact that fat and water have different phase positions at different echo times.

Depending on application these two approaches have different advantages or disadvantages, and the radiologists performing the examination often have different preferences. Each of the methods has advantages and disadvantages, wherein each of the two methods is not applicable in every situation.

Newer MRT systems aim to make these accessible for customer groups who have previously not used MRT devices. For these customer groups it is often difficult to find well-trained MR operating personnel. As mentioned above, many adjustment options exist for creating different contrasts. Well-trained operators are necessary for this. The operator is interested in having a simple design of operating interface, in further automations such as for example the automated selection of a slice position to create the MR images or in the selection of the Field of View, FOV.

As mentioned above, a certain level of expert knowledge is needed to choose a suitable fat suppression mode, since the best choice depends on a variety of factors.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 2 shows different options of the basis that operate for the different suppression options according to an exemplary embodiment.

FIG. 3 illustrates a flowchart of a method for automatic selection of a suppression option for an imaging sequence according to an exemplary embodiment.

FIG. 4 illustrates a flowchart of a method to select of one of the two suppression options according to an exemplary embodiment.

Figure 1:
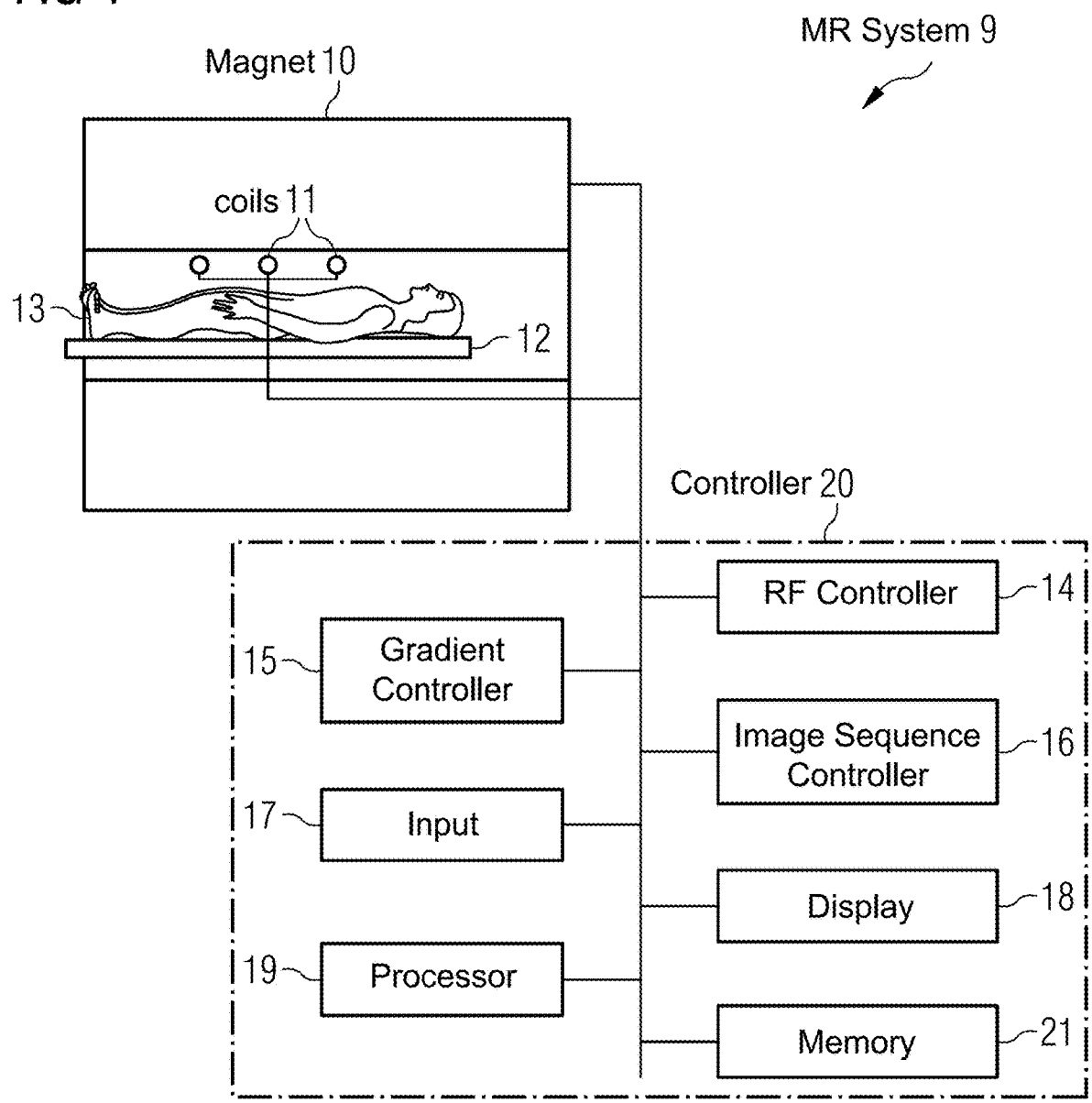
FIG. 1 shows a schematic of an MR system according to an exemplary embodiment that is configured to select an option for suppression of a tissue component is simplified.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the present disclosure is to further simplify the selection of the suppression of a tissue component that is not wanted in the MR signal.

In an aspect of the disclosure, a method is provided for automatic control of an examination sequence in an MR system during the recording of MR signals in an examination segment of a person being examined. The examination segment has two tissue components with two different MR resonant frequencies. In this automatic method the sequence of the examination for the examination of the examination segment is determined. It is further determined whether the examination features an imaging sequence in which one of the two tissue components is to be suppressed and for which at least two different examination options exist for reducing a tissue component during the MR signal recording. If this is the case, a sequence parameter of the examination is determined and one of the two suppression options is selected automatically for the imaging sequence as a function of the sequence parameter determined.

The determination of the sequence parameter means that a variable is available that is used to select one of the at least two suppression options. The user is thus freed from this task and the system can select the best suppression option automatically for the present situation and the present examination. This can mean that the associated imaging sequences also differ since the two options utilize different effects and therefore different sequences of gradients and RF pulses can be necessary.

The at least two different suppression options feature a first suppression option, in which the two tissue components are excited differently with a spectrally selective RF pulse, wherein the second suppression option uses the different phase position of the two tissue components during one or more echo times.

An inhomogeneity parameter can be determined with the MR system during the determination of the sequence parameter for example. This inhomogeneity parameter is then used automatically to select one of the two suppression options automatically.

The inhomogeneity parameter can include a homogeneity of the polarization field $B_0$, a homogeneity of the $B_1$ field for radiating RF pulses in during the imaging sequence and/or a size of the induced eddy current.

If for example the inhomogeneity parameter is greater than a defined limit value, the system can automatically uses the second suppression option, which is based on the DIXON method. The DIXON method has the advantage of being more robust in relation to inhomogeneities, of the $B_0$ field for example, in eddy currents or of the $B_1$ field. For greater inhomogeneities it is difficult to separate spectral components that lie close to one another in such a way that the one is excited and the other not, as is necessary for the first option.

A further sequence parameter that can be determined is the distance from a center of the MR system, at which the examination segment is positioned during the recording of the MR signals. This distance can likewise be taken into account in the automatic selection of one of the two suppression options.

If for example the distance from the center is greater than a limit value, then preferably the second suppression option, which is based on the DIXON method, can be used. For measurements that are carried out outside the center of the MR system, the homogeneity of fields needed is often not good enough for a spectral saturation to be satisfactorily possible. Therefore it is advantageous here to select the suppression option in which the different phase position of the two tissue components are used to separate the two signal components.

The first suppression option with the use of a spectrally selective RF pulse can be used when the inhomogeneity parameter is less that a limit value and when the distance from the center is less than a further limit value. The limit value for the inhomogeneity parameter can lie at 20, 25 or 30% of the spectral difference between the two components, thus for fat and water at 0.25*3.5 ppm for example. The limit value for the distance from the center, measured at the greatest possible field of view, FOVmax, can lie at 30, 40, 50 or 60% of FOVmax.

If on the other hand for one of the two parameters, the distance from the center is greater than the limit value or the inhomogeneity parameter is greater than a further limit value, then the second suppression option according to the DIXON method can be used.

It is furthermore possible to store the at least two different suppression options in connection with the imaging sequence. When the imaging sequence is selected for the examination sequence then there is also the knowledge that the two different suppression options are possible and that a choice must be made here.

The automatically selected suppression option can be displayed here so that it can be confirmed by the operator, or the MR signals are recorded automatically with the selected suppression option.

An MR system is furthermore provided, which is embodied as explained above or explained below. The MR system has a controller, which is embodied to carry out the method according to the exemplary embodiments and other aspects of the disclosure.

In addition, a computer program is provided with program means that can be loaded directly into a memory of a controller of the MR system, in order to carry out the steps of the method described above or described below when the program means are executed in the controller.

Likewise, an electronically readable data medium is provided with electronically readable control information stored thereon. This is designed so that, when the data medium is used in a controller of the MR system, it carries out the method described above or below.

FIG. 1 illustrates a Magnetic Resonance (MR) system 9 according to an exemplary embodiment. In an exemplary embodiment, the MR system 9 is configured for a simplified selection of a suppression of a tissue component for the recording of the MR signals. In an exemplary embodiment, the MR system 9 has a magnet 10 for creating a position field $B_0$, wherein a person being examined 13 arranged lying on a couch 12 is moved into the magnet, in order for spatially encoded magnetic resonance signals to be recorded there from a specific examination segment of the person 13. Coils 11 for recording the MR signals are shown schematically, which can be embodied as whole-body coils or local coils. Radiating in radio-frequency pulses and switching magnetic field gradients enables the magnetization created by the polarization field $B_0$ deflected from the equilibrium position to be spatially encoded, and the magnetization produced by the receive coils 11 to be detected. How MR images can be created by radiating in RF pulses and by switching the magnetic field gradients in different combinations and sequences is basically known to the person skilled in the art and will not be explained in any greater detail here for brevity.

In an exemplary embodiment, the MR system 9 further includes a controller 20, which is configured to control of the MR system 9. The controller 20 has an RF controller 14 configured to control and generate the RF pulses for deflection of the magnetization. Furthermore a gradient controller 15 is provided configured to control and switch the necessary magnetic field gradients. An image sequence controller 16 is configured to control the order of the magnetic field gradients, the signal detection and the RF pulses and thus also the gradient controller 15, the receive coils and the RF controller 14. An operator can control the MR system 9 via an input 17, and MR images and other information necessary for control can be displayed on a display 18.

The MR system 9 further includes a processor 19 configured to control of the different units in the controller 20. Furthermore, a memory 21 is provided, in which for example program modules or programs can be stored, which, when they are executed by the processor 19, can control the execution sequence of the MR system. The controller 20 or the processor 19 can be configured, as explained below, to determine from the examination sequence determined whether a tissue component is to be suppressed in an imaging sequence. If this is the case one of the possible suppression options is selected automatically. In an exemplary embodiment, the controller 20 (and/or one or more components of the controller 20) includes processor circuitry that is configured to perform one or more corresponding functions and/or operations of the controller 20 (and/or components therein).

The explanation below is given with the aid of the two tissue components fat and water. It is however possible to apply the method described for other different tissue components such as fat and silicon, water and silicon etc. The method described below represents a method that automatically suggests the fat suppression mode to be used to the operator or which automatically sets the selected suppression option. System characteristics of the MR system and location of the examination segment can be taken into consideration in the MR system.

FIG. 2 shows a schematic of a spectrum 20 with the two maxima 21 and 22 according to an exemplary embodiment. In this example, the maximum 21 stands for the fat signal and the maximum 22 for the water signal. Both components have an approximate frequency difference of 3.5 ppm (parts per million). If the homogeneity of the MR components of the MR system 9 is now good enough for one of the two components to be able to be excited spectrally selectively, then it is possible to excite the tissue component to be suppressed on its own, so that this no longer delivers a signal later during the recording of the MR signals. The excitation takes place either with the subsequent application of a gradient pulse in order to scatter the phase position of the excited component, so that an MR signal is no longer present, or the other further option consists of exciting a spectral component selectively and selecting the signal readout such that the excited component no longer has a signal portion in the signal readout.

Shown schematically in the lower part is the other suppression option, which is referred to below as the second suppression option. Through the different resonant frequency the two components fat and water have different phase positions as a function of the echo time. For example at a first time TE1 both components can have the same phase position while during a second echo time TE2 the two components can have a different, opposed phase position. By using the signals from at least one of the two echo times it is possible to determine the influence of the individual components individually, as is known from the different DIXON methods.

In an exemplary embodiment, the method includes the following steps:

In a first step a measurement protocol is started, meaning that it is determined from the examination sequence which imaging sequences will be used to create the MR images in order to address a particular medical issue. In this start of the examination sequence slices can be proposed automatically or the location of the slices relative to the examination object, the size of the field of view etc. Furthermore there is usually a so-called shim or tuning procedure at the beginning so that the homogeneity, the $B_0$ field, the $B_1$ field with which the measurement is executed is known. In addition the location of the examination segment relative to the MR system is known thereby, namely whether the examination segment is located exactly in the isocenter of the MR system or more at the edge of the field in which MR signals can be recorded.

In a second step a check is made for all protocol steps of the examination sequence as to whether a saturation of a component such as for example a fat suppression is to be used. If this is the case, the optimal suppression option is established and the appropriate sequence protocol for the application is taken from a database that is stored in the memory 21 for example. For the different medical issues such as for example knee measurements or thorax measurements, the suppression options in question can be stored in the database for the contrast needed. In an exemplary embodiment, the following information can be taken into consideration in the choice of suppression mode:

The system characteristics and imperfections of the MR system can be taken into account. These comprise eddy current thermals, $B_0$ and/or $B_1$ inhomogeneities. These characteristics differ from MR system to MR system and depend on many factors such as the geometry of the examination segment. These characteristics and inhomogeneities are usually known at the start of the actual MR measurement for example since these are determined and optimized if necessary in a tuning mode at the beginning before the start of the actual MR measurement.

In addition the location of the examination segment in relation to the isocenter and the coverage needed can be determined, meaning the size of the field of view. This information can either be predetermined by the operator or can be taken from the above step for automatic sequences.

It is now determined from the combination of these two factors whether the segment still lies in an area in which a spectral saturation by means of an RF pulse is possible. Since the inhomogeneities mentioned above generally increase as the distance from the isocenter increases, as from a specific distance for example there can be an automatic switch to the suppression option that uses the different phase position according to DIXON. The frequency errors caused by eddy currents or field inhomogeneities lie in the outer areas of the MR system in a range that corresponds to the spectral difference between fat and water. The distance from the isocenter can be determined here as a relative value, e.g., as a percentage of the maximum possible field of view. If for example the measurement area lies in a segment that lies below 50, 60 or 70% of the maximum field of view, then the spectral saturation is selected in this way and outside this range the DIXON method.

In the example of a knee examination, this would mean that the suppression option and thus the imaging sequences to be used are determined on the basis of the location and the extent of the knee and the eddy currents, the $B_0$ inhomogeneities or $B_1$ inhomogeneities.

In a third step, the sequence now determined in this way is either suggested to the operator or automatically integrated into the examination sequence, so that the method can execute without any interaction with the operator.

Furthermore, the method can also be embodied in such a way that, depending on the aforementioned parameters such as the distance from the center and the inhomogeneities, only specific suppression options are allowed or able to be selected. For example in areas with known very high eddy currents that would not allow a suppression option with spectral saturation. Here the operator already sees from the presentation of the examination sequence that in the present example no spectral fat saturation can be possible.

FIG. 3 illustrates a flowchart of a method according to an exemplary embodiment. The method starts in a step S31 and in a step S32 the examination sequence is defined for the person being examined, wherein it is determined here that recordings in a specific part of the body such as knee, shoulder or head area are necessary. In a step S33 it is investigated whether an imaging sequence will be used for the examination sequence for which different suppression options are possible for the suppression of a tissue component and a suppression is desired. This is possible since for example the theoretically possible suppression options that are able to be selected for each imaging sequence are stored in the memory. If it is established in step S33 that such an imaging sequence is to be used, then in step S34 the sequence parameter of the examination is determined. In the examples given above the sequence parameter contains a parameter about the inhomogeneity and/or a parameter about the distance from the isocenter. When one or more of these parameters is determined then it can be determined as a function of one or more of these parameters which suppression option will be selected in step S35. Finally, in step 36 the imaging sequence is recorded with the corresponding suppression option. If it is determined in step S33 that no options exist for the choice of the suppression options, in step S37 the imaging sequence in accordance with the selected examination sequence without the option for suppression of a tissue component is selected. The method ends in step S38.

The determination of the sequence parameter from step S34 is explained in greater detail in FIG. 4. In step S41 the parameter that is an inhomogeneity parameter can be determined here and the inhomogeneities of the components of the MR system defined, such as for example the inhomogeneity of the $B_0$ field or the eddy currents to be expected. Furthermore, in a step S42, a check is made as to the distance from the isocenter at which the signals are to be recorded. This can be determined from the selected slice position. These two parameters can now be used together, in order finally, in a step S43, to select one of the two suppression options as explained above. If the distance is less than a limit value and if the inhomogeneity is less than a limit value, the first option can be selected. Otherwise the second option is selected.

The exemplary embodiments of the disclosure provide an automatic selection of an advantageous optional suppression of a tissue component, where system characteristics such as location and the physiology of the person being examined are taken into account.

Above all, for inexperienced users, the method offers the advantage that the choice and the necessary understanding for the selection of the suitable imaging sequence is taken away from them without them having to exert any influence on it. This enables errors in artifacts in the images to be avoided, which would make a new examination necessary for example.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for automatic control of an examination sequence in magnetic resonance (MR) system during recording of MR signals in an examination segment of a person being examined, which has two tissue components with two different MR resonant frequencies, the method comprising:
  determining an examination sequence for examination of the examination segment; and
  determining whether the examination sequence includes an imaging sequence in which one of the two tissue components is to be suppressed and for which at least two different suppression options exist to reduce the one of the two tissue components during the recording of the MR signals, wherein, in response to the examination sequencing including the imaging sequence:
    determining one or more sequence parameters of the examination for the imaging sequence, wherein the determination of the one or more sequence parameters includes:

determining at least one inhomogeneity parameter of the MR system including a size of an induced eddy current; and determining a field-of-view (FOV) factor and a maximum FOV; and automatically selecting one of the at least two suppression options as a function of based on the determined at least one inhomogeneity parameter, the FOV factor, and the maximum FOV.

2. The method as claimed in claim 1, wherein the at least one inhomogeneity parameter further includes at least one of the following parameters: a homogeneity of a polarization field $B_0$, and a homogeneity of a $B_1$ field for radiating radio frequency (RF) pulses into the examination segment.

3. The method as claimed in claim 1, wherein the at least two different suppression options include a first suppression option, in which the two tissue components are excited differently with a spectrally selective radio frequency (RF) pulse, and a second suppression option in which a different phase position of the two tissue components at an echo time is used.

4. The method as claimed in claim 1, wherein:
the at least two different suppression options include a first suppression option, in which the two tissue components are excited differently with a spectrally selective radio frequency (RF) pulse, and a second suppression option in which a different phase position of the two tissue components at an echo time is used; and
the second suppression option is selected in response to the inhomogeneity parameter being greater than a first limit value.

5. The method as claimed in claim 4, wherein the second suppression option is selected in response to either a distance from a center of the MR system being greater than a second limit value or the inhomogeneity parameter being greater than a first limit value.

6. The method as claimed in claim 1, wherein the at least two different suppression options are stored and linked to the imaging sequence.

7. The method as claimed in claim 1, further comprising displaying, on a display, the selected one of the at least two suppression options as a confirmation for an operator controlling the sequence of the examination.

8. The method as claimed in claim 1, further comprising automatically recording the MR signals from the examination segment with the imaging sequence and the selected one of the at least two suppression options.

9. A non-transitory computer-readable storage medium with an executable program stored thereon, that when executed, instructs a processor to perform the method of claim 1.

10. The method as claimed in claim 1, wherein the determination of the one or more sequence parameters further includes determining a distance at which the examination segment is positioned from a center of the MR system during the recording of the MR signals, the distance being determined based on the FOV factor and the maximum FOV, wherein the one of the at least two suppression options is selected automatically based on the determined distance.

11. The method as claimed in claim 10, wherein:
the at least two different suppression options include a first suppression option, in which the two tissue components are excited differently with a spectrally selective radio frequency (RF) pulse, and a second suppression option in which a different phase position of the two tissue components at an echo time is used; and the second suppression option selected in response to the distance from the center being greater than a first limit value.

12. The method as claimed in claim 11, wherein the first suppression option is selected in response to the inhomogeneity parameter being less than a second limit value and the distance being less than the first limit value.

13. The method as claimed in claim 10, wherein:
the at least two different suppression options include a first suppression option and a second suppression option;
the first suppression option is selected in response to the inhomogeneity parameter being less than a second limit value and the distance being less than a first limit value; and
the second suppression option is selected in response to either the distance from the center being greater than the first limit value or the inhomogeneity parameter being greater than the second limit value.

14. The method as claimed in claim 13, wherein first suppression option includes the two tissue components being excited differently with a spectrally selective radio frequency (RF) pulse, and the second suppression option includes a different phase position of the two tissue components at an echo time being used.

15. The method as claimed in claim 10, wherein the at least two different suppression options include a first suppression option, in which the two tissue components are excited differently with a spectrally selective radio frequency (RF) pulse, and a second suppression option in which a different phase position of the two tissue components at an echo time is used.

16. The method as claimed in claim 1, wherein:
the determination of the one or more sequence parameters further comprises determining a distance at which the examination segment is positioned from a center of the MR system during the recording of the MR signals; and
the method further comprises comparing the distance to a limit value, wherein the one of the at least two suppression options is selected automatically further based on the comparison, the limit value being determined based on the FOV factor and the maximum FOV.

17. A magnetic resonance (MR) system configured to automatically control an examination sequence during recording of MR signals in an examination segment of a person being examined, which has two tissue components with two different MR resonant frequencies, the MR system comprising:
a MR scanner configured to record the MR signals; and
a controller that is configured to:
determine the examination sequence for examination of the examination segment; and
determine whether the examination sequence includes an imaging sequence in which one of the two tissue components is to be suppressed and for which at least two different suppression options exist to reduce the one of the two tissue components during the recording of the MR signals, wherein, in response to the examination sequencing including the imaging sequence:
determining one or more sequence parameters of the examination for the imaging sequence, wherein the determination of the one or more sequence parameters includes: determining at least one inhomogeneity parameter of the MR system including a size of an induced eddy current, and determining a field-of-view (FOV) factor and a maximum FOV; and automatically selecting one of the at least two suppression options based on the at least one inhomogeneity parameter, the FOV factor, and the maximum FOV.

18. The system as claimed in claim 17, wherein the determination of the one or more sequence parameters further includes determining a distance at which the examination segment is positioned from a center of the MR system during the recording of the MR signals, the distance being determined based on the FOY factor and a maximum FOV, wherein the one of the at least two suppression options being selected automatically based on the determined distance.

19. The system as claimed in claim 18, wherein:

the at least two different suppression options include a first suppression option and a second suppression option;

the first suppression option is selected in response to the inhomogeneity parameter being less than a second limit value and the distance being less than a first limit value; and the second suppression option is selected in response to either the distance from the center being greater than the first limit value or the inhomogeneity parameter being greater than the second limit value.

20. The system as claimed in claim 17, wherein the at least one inhomogeneity parameter further includes at least one of the following parameters: a homogeneity of a polarization field $B_0$, and a homogeneity of a $B_1$ field for radiating radio frequency (RF) pulses into the examination segment.

* * * * *